United States Patent [19]

Olesen et al.

[11] Plant 5,058

[45] Jun. 7, 1983

[54] MINIATURE ROSE PLANT — POULFI VARIETY

[75] Inventors: Mogens Olesen; Pernille Olesen, both of Kvistgaard, Denmark

[73] Assignee: The Conard-Pyle Company, West Grove, Pa.

[21] Appl. No.: 320,672

[22] Filed: Nov. 12, 1981

[51] Int. Cl.[3] ..... A01H 5/00
[52] U.S. Cl. ..... Plt./9
[58] Field of Search ..... Plt./9

*Primary Examiner*—James R. Feyrer

*Attorney, Agent, or Firm*—Burns, Doane, Swecker & Mathis

[57] ABSTRACT

A new and distinct variety of rose plant of the Miniature Class is provided which originated by crossing an unnamed and unpatented Miniature rose seedling with the variety Harriet Poulsen (unpatented) of the Floribunda Class. This new variety has a dwarf growth habit and abundantly forms attractive bright fluorescent pink flowers which are semi-double and borne in clusters. Plants of the new variety are particularly suited for growing in planters or window boxes and also are well adapted to greenhouse forcing.

1 Drawing Figure

SUMMARY OF THE INVENTION

The present variety relates to a new and distinct variety of rose plant of the Miniature Class which was originated by us by crossing an unnamed and unpatented Miniature rose seed parent and a pollen parent of the Floribunda variety Harriet Poulsen (unpatented). The Harriet Poulsen variety had as its parents the Mme. Norbert Levavasseur and Dorothy Perkins varieties (both unpatented).

As a result of this breeding, we have produced a new and improved rose variety of the Miniature Class which is distinguished from its parents, as well as all other varieties of which we are aware, as evidenced by the following unique combination of characteristics which are outstanding therein:

(a) a micromini growth habit which forms a low and compact plant,
(b) the exhibition of more plant vigor than an average rose plant of the Miniature Class,
(c) the formation of buds which are relatively long in configuration, and
(d) the abundant formation in clusters of semi-double bright fluorescent pink flowers.

When compared to its unnamed seed parent, our new variety exhibits a dissimilar symmetrical micromini growth habit which is lacking in the parent.

When compared to its pollen parent of the Harriet Poulsen variety, our new variety exhibits semi-double flowers, while this parent exhibits only single flowers. Also the bright pink flowers of the new variety are quite different in color from the apple-blossom pink flowers of this parent.

Plants of the new variety grow well in planters and in window boxes, and are well adapted for greenhouse forcing. The new variety can be considered a prolific bloomer.

Asexual reproduction of the new variety by budding and by cuttings, as performed in Denmark and at West Grove, Pa., U.S.A., shows that the aforementioned characteristics and distinctions come true to form and are established and transmitted through succeeding propagations. Such asexual reproduction may be accomplished readily with the use of cuttings.

The new variety has been named the Poulfi variety.

BRIEF DESCRIPTION OF THE PHOTOGRAPH

The accompanying photograph shows typical specimens of the vegetative growth and flowers of my new variety in different stages of development following cultivation in the outdoors at West Grove, Pa. during September, as depicted in color as nearly true as is reasonably possible to make the same in a color illustration of this character.

DETAILED DESCRIPTION OF THE DISCLOSURE

The plants described were grown outdoors at West Grove, Pa. during September.

The chart used in the identification of the colors is that of The Royal Horticultural Society (R.H.S. Colour Chart).

Class: Miniature (micro).

Branches:

*Color.*—New shoots, Yellow-Green Group 146C with reddish overcast. Young stems, bright, Yellow-Green Group 146B. Main stems, bright Yellow-Green Group 146B.

*Thorns.*—Young stems, few with reddish cast. Main stems, present in moderate amounts with reddish cast.

Foliage:

*Leaves.*—Compound of usually 5 leaflets, moderately abundant, leathery.

*Leaflets.*—Ovate, obtuse apex, obtuse base, and a serrulate margin. Color: new shoot foliage: Yellow-Green Group 146B with shades of Red-Purple Group 59B. Color: young foliage: Upper surface: Yellow-Green Group 146B with top edges Red-Purple Group 59B. Under surface: Yellow-Green Group 146C to 146D. Color: mature foliage: Upper surface: Yellow-Green Group 147B with shades of Yellow-Green Group 148B. Under surface: Yellow-Green Group 146B to 146C.

Flowers:

*Number of flowers.*—Several semi-double flowers per stem forming clusters on shorter stems of normal strength.

*Quantity of bloom.*—Abundant outdoors.

*Fragrance.*—Very slight.

*Continuity.*—Continuous.

*Opening.*—Opens up well.

*Peduncle.*—Short, slender, erect, with few reddish tipped hairs, length of approximately 0.9 mm. to 1.1 cm. before calyx breaks.

*Sepals.*—Permanent, short to medium length, spear shaped.

*Bud.*—Shape: ovoid, conspicuous neck, foliaceous appendages on the surface of the bud, and small foliaceous parts extending beyond the tip of the bud equal to ¼ or more of its length. Size: average length of approximately 1.6 to 2.6 cm. Color: as calyx breaks: base of inner and outer petal Yellow-Green Group 154B changing to Red-Purple Group 57D with tones ranging to 53C. Color: as first petal opens: the point of attachment and base of petal in Yellow-Green Group 154C with shades of 154B, with remainder of the petal being Red-Purple Group ranging from 57B to 57D on the outside and from 58B to 58C on the inside.

*Bloom.*—Size when fully open: averages from approximately 2.9 to 3.3 cm. Petalage: semi-double, approximately 16 to 19 petals arranged regularly, petals are obovate, soft and thin, and satiny. Form: high centered at first but becoming flat, petals being at first loosely cupped outward and remaining loosely cupped outward at maturity. Color: newly opened, outer petal — outside surface: base of petal is Yellow-Green Group 8D changing abruptly to Red-Purple Group 57D mixed with shades of 57C. Color: newly opened, outer petal — inside surface: base of petal is Yellow Group 8D changing abruptly to Red-Purple Group 63C in the middle with color ranging to 63A at the tip. Color: newly opened, intermediate petal — outside surface: base of petal is Yellow Group 8D with slight tones of Yellow Group 8C changing to Red-Purple Group 63B with shades of 63A. Color: newly opened, intermediate petal — inside surface: inner base of petal is Yellow Group 8D with slight tones of Yellow Group 8C changing to Red-Purple Group 63C with shades of 63A and 63B. Color: newly opened, inner petal — outside surface: base of petal extending in a straight line to tip of petal is Yellow Group 8D, and remainder of petal is Red-Purple Group 57D ranging to 57B. Color: newly opened inner petal — inside surface: base and center of base to tip of petal is Yellow Group 8D, and remainder of petal is Red-Purple Group 63C with shades of 63A and 63B. Color: fully open, outer petal — outside surface: base of petal at point of attachment is Yellow Group 8A ranging to 8D, and remainder of petal ranges from Red-Purple Group 57B to 57D. Color: fully open, outer petal — inside surface: base of petal Yellow Group 8A ranging to 8D, and remainder of petal ranges from Red-Purple Group 57D to 58A. Color: fully open, inner petal — outside surface: base of petal at point of attachment and along line going up the center is Yellow Group 8D with shades of 8C, and remainder of petal ranges from Red-Purple Group 58D to 63B. Color: fully open, inner petal — inside surface: base of petal at point of attachment Yellow Group 8D, and remainder of petal is Red-Purple Group 63C with tones of 63A. General color effect: the general effect of the fully open bloom is Yellow Group 8A ranging to 8D at point of attachment, and remainder of petal has tones of Red-Purple Group 57B through 57D. Flower longevity: on the bush in garden approximately 4 to 7 days from calyx break to color breakdown or dropping of the petals. Stamens: medium number, mostly arranged regularly, mixed with petaloids. Filaments: short, most with anthers, Yellow-White Group 158A in color. Anthers: very small, Greyed-Orange Group 165B in color. Pistils: medium number. Styles: uneven, short, columnar. Stigma: Greyed-Yellow Group 160B in color. Hips: average size of 0.07 mm. to 1.1 cm., smooth, glandular, medium thickness, fleshy, Yellow-Green Group 146D in color. Seeds: few, small.

Disease resistance: Resistance comparable to that of the average variety growing under the same cultural conditions.

Growth:

*Habit.*—Dwarf, upright.

*Growth.*—Free.

*Canes.*—Light.

Usage: The variety is particularly suited for growing in planters and window boxes, and is also well adapted for growing indoors under light.

We claim:

1. A new and distinct variety of rose plant of the Miniature Class, substantially as herein shown and described, characterized particularly by (a) a micromini growth habit which forms a low and compact plant, (b) the exhibition of more plant vigor than an average rose plant of the Miniature Class, (c) the formation of buds which are relatively long in configuration, and (d) the abundant formation of clusters of semi-double bright fluorescent pink flowers.

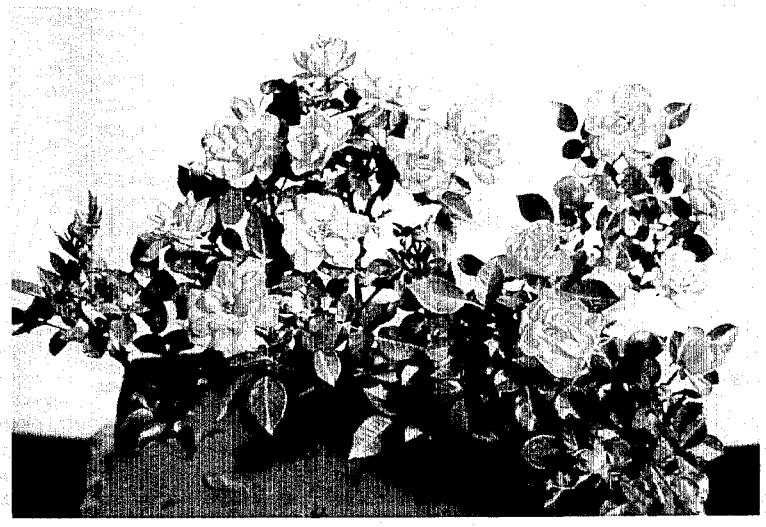

* * * * *